(12) United States Patent
Amagase et al.

(10) Patent No.: US 8,728,547 B2
(45) Date of Patent: May 20, 2014

(54) FORMULATIONS AND METHODS FOR INCREASING METABOLIC RATE AND WEIGHT CONTROL

(75) Inventors: Harunobu Amagase, Phoenix, AZ (US); Richard Handel, Little Falls, NJ (US)

(73) Assignee: Freelife International, Inc., Phoenix, AZ (US)

(*) Notice: Subject to any disclaimer, the term of this patent is extended or adjusted under 35 U.S.C. 154(b) by 137 days.

(21) Appl. No.: 13/139,006

(22) PCT Filed: Feb. 5, 2009

(86) PCT No.: PCT/US2009/033224
§ 371 (c)(1),
(2), (4) Date: Jun. 10, 2011

(87) PCT Pub. No.: WO2010/068305
PCT Pub. Date: Jun. 17, 2010

(65) Prior Publication Data
US 2011/0244061 A1  Oct. 6, 2011

Related U.S. Application Data

(60) Provisional application No. 61/121,519, filed on Dec. 10, 2008.

(51) Int. Cl.
*A61K 36/82* (2006.01)

(52) U.S. Cl.
USPC ............ 424/729; 514/567; 544/274; 562/445

(58) Field of Classification Search
None
See application file for complete search history.

(56) References Cited

U.S. PATENT DOCUMENTS

| | | | |
|---|---|---|---|
| 7,030,092 B1 | 4/2006 | Levine | |
| 7,074,440 B2 * | 7/2006 | Xiu | ............... 424/728 |
| 2007/0212433 A1 | 9/2007 | Smidt et al. | |
| 2007/0292560 A1 * | 12/2007 | Quan et al. | ......... 426/3 |

OTHER PUBLICATIONS

International Search Report and Written Opinion as mailed on Mar. 26, 2009 for International Application No. PCT/US2009/033224.

* cited by examiner

*Primary Examiner* — Susan Hoffman
(74) *Attorney, Agent, or Firm* — Quarles & Brady LLP

(57) ABSTRACT

The invention provides methods for increasing resting metabolic rate, reducing waist circumference, and weight control by administering a composition comprising dietary fiber, phenylalanine, tyrosine, tea blend, caffeine, and *Lycium* plants or *Lycium* plant extract preparations to the subject. The invention also provides a food or dietary supplement formulation which contains dietary fiber, phenylalanine, tyrosine, tea blend, caffeine, and *Lycium* plants or *Lycium* plant extract preparations.

4 Claims, 2 Drawing Sheets

FORMULATIONS AND METHODS FOR INCREASING METABOLIC RATE AND WEIGHT CONTROL

CROSS-REFERENCES TO RELATED APPLICATIONS

This application represents the U.S. national phase entry of PCT International Application No. PCT/US2009/033224 filed Feb. 5, 2009, which claims the benefit of U.S. Provisional Patent Application Ser. No. 61/121,519, filed on Dec. 10, 2008, all of which are incorporated herein by reference for all purposes.

FIELD OF THE INVENTION

The invention relates generally to formulations and methods for increasing metabolic rate and achieving weight control in mammals.

BACKGROUND OF THE INVENTION

Low metabolic rate is strongly related to obesity and is a strong risk factor for heart attacks, strokes, diabetes and other diseases. Based on new research, increased metabolic rate or thermogenesis is connected to weight loss.

Many people are advised to eat less, to avoid calorie-dense foods that are high in fat and/or sugar, and to increase their intake of foods such as fruits, vegetables and whole grains, which are filling but not fattening. Physical activity should also be incorporated into daily life.

Tea and caffeine consumption is known to increase thermogenesis in the body and help people lose weight. However, high caffeine consumption can lead to addiction and is related to headache and other physical symptoms. And, while many people have heard the above suggestions from doctors and physical practitioners, it is often difficult to change one's life style. As a result, the number of obese subjects is rising sharply. Accordingly, a need exists for compositions and methods of increasing metabolic rate and reducing weight in subjects which avoids invasive and rigorous intervention.

SUMMARY OF THE INVENTION

Here, the inventors demonstrate versatile formulations and methods for total weight control through increased metabolic rate and reducing waist circumference.

Accordingly, the present invention provides a method of weight control in a subject, the method comprising administering a composition consisting of dietary fiber, phenylalanine, tyrosine, tea blend (green, black, Oolong, white and any other tea), caffeine, and *Lycium* plants (known as goji, gouqizi, Fructus lycii or wolfberry) or *Lycium* plant extract preparations, whereby the subject's resting metabolic rate is increased such that said subject achieves weight control. In an alternate preferred embodiment, the composition comprises a juice formula.

In another embodiment, the invention provides a method of weight control in a subject, the method comprising administering a composition comprising dietary fiber, phenylalanine, tyrosine, tea blend, caffeine, and *Lycium* plants or *Lycium* plant extract preparations, whereby the subject's waist circumference is reduced such that said subject achieves weight control. In an alternate preferred embodiment, the composition comprises a juice formula.

In yet another embodiment, the invention provides a food or dietary supplement formulation comprising an effective amount of dietary fiber, phenylalanine, tyrosine, tea blend, caffeine, and *Lycium* plants or *Lycium* plant extract preparations and at least one other food or dietary supplement ingredient. In an alternate preferred embodiment, the composition comprises a juice formula.

The invention also encompasses the use of dietary fiber, phenylalanine, tyrosine, tea blend, caffeine, and *Lycium* plants or *Lycium* plant extract preparations, preferably goji juice, for the manufacture of food formulations to increase resting metabolic rate, reduce waist circumference, and achieve weight control in a subject ingesting the food formulation. *Lycium* plants or *Lycium* plant preparations, preferably goji juice, packaged and presented for use in the increase of metabolic rate and reduction of waist circumference are also within the invention.

Other objects, features and advantages of the present invention will become apparent after review of the specification, claims and drawings.

DETAILED DESCRIPTION OF THE INVENTION

I. In General

Figure 1:
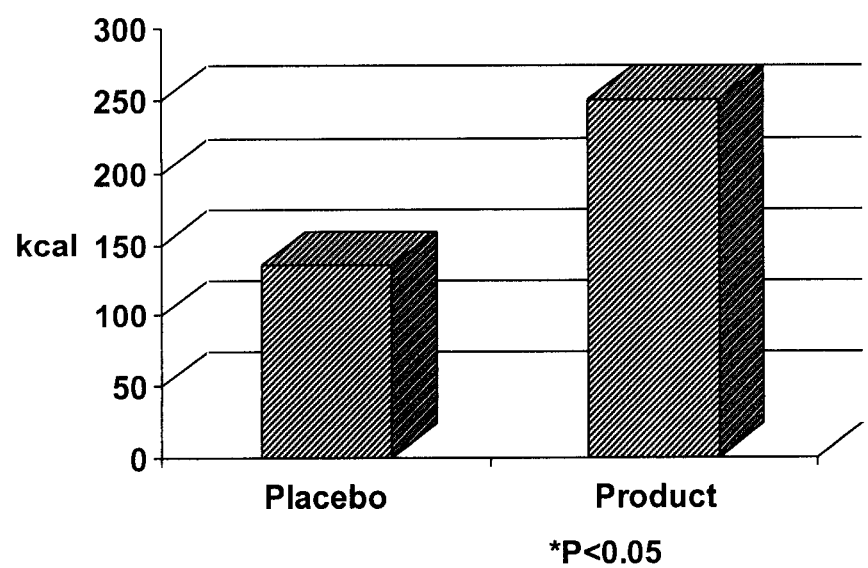
FIG. 1. Changes in resting metabolic rate on Day 8 two hours after consumption or placebo or Product.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed non-provisional applications.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

Herein, the inventors provide formulations and methods for weight control by increased resting metabolic rate and reducing waist circumference in mammals.

The Product is formulated from a mixture of dietary fiber, phenylalanine, tyrosine, tea blend, caffeine, and *Lycium* plants or *Lycium* plant extract preparations, preferably goji juice. The term "Product" as used herein refers to a formulation according to the present invention.

Although the Product contains similar ingredients to tea and coffee (polyphenol and caffeine), the Product unexpectedly provides much greater weight control benefits than a cup of tea or coffee. The Product begins to increase metabolic rate within ten minutes of consumption and the effect lasts longer than four hours. On the other hand, a cup of strong green tea only slowly increases metabolic rate, and the effect is short-lived, disappearing within one hour. Thus, this new formula has a much better effect on metabolic rate when used for weight control than a cup of tea.

Although increased daily consumption of dietary fiber is strongly recommended by government agencies and researchers, the public has not responded to these recommendations. Consuming more than 10 grams of fiber a day (half of the daily recommendation) is difficult for many people, especially when consumed in powder form. In this invention, we developed a liquid form of the Product which contains five grams of indigestible fiber in a comfortable dosage form. In the case of powders, capsules, or tablets, it is difficult to take such a high amount of fiber at one time. Liquid is the preferred way to absorb bioavailable ingredients quickly.

Phenylalanine and N-acetyl-L-tyrosine are a part of essential amino acids; however, it is not possible to consume the recommended amount of these through regular food consumption. The Product was formulated with these two amino acids for effective appetite control. The liquid form of the Product supplies the recommended amount of these amino acids.

Green, black, oolong, and white tea are combined to maximize the effects of the tea. As different tea contains different ingredients, our invented tea blend has variety of active ingredients, which are especially good for thermogenesis which indicates an increase in metabolic rate.

The *Lycium* plants in this invention are the plants belonging to the family of solanaceous defoliated shrubbery, such as, *Lycium barbarum* and *Lycium chinensis*. The most suitable plant for this invention is *Lycium barbarum* (known as goji, gouqizi, fructus lycii, or wolfberry). The preferred portion for this invention is the fruit of this plant. The leaf, root or stem may also be utilized for this invention. These materials can be processed as juice or dried by processing and/or extraction methods commonly known in the art.

In addition, the materials derived from the cell culture of the plants can also be utilized for this invention. The juice or extract of the tea or *Lycium* plants in this invention is preferably the preparation made from plant materials prepared or extracted from water or alcohol. The tea or *Lycium* plants for the preparation or extraction can be squeezed or crushed with or without heating to effect extraction efficiency, as is routinely understood in the art. It is also possible to crush and homogenize the plants to make the juice after separating the skin, seeds, and other parts. The extract prepared for dietary intake can be utilized as is, in concentrated fluid, or in powder form after concentration under vacuum or lyophilization.

The administrative dosage of the preparation effective to control weight through the various mechanisms incorporated in this invention depends on the ingredients, age, and body weight or body condition of the human subject. It is recommended that adults orally consume 0.01 oz (0.3 ml) through 33 oz (990 ml) of a liquid preparation of the combination of dietary fiber, tea blend, Phenylalanine, N-acetyl-L-tyrosine, caffeine, and *Lycium* plants or extracted *Lycium* plants daily.

The more feasible and preferred dosage ranges approximately from 1 oz (30 ml) to 8 oz (240 ml) of the preparation per day for an adult human.

The range for each ingredient is preferably:

Dietary fiber: 0.1 g to 100 g per day. Any sources are applicable for this invention, but preferably corn-derived indigestible soluble fiber is used.

Tea blend: 0.001 g to 100,000 g per day. Any teas can be blended together. This invention is not limited to green, black, white, and oolong tea.

Phenylalanine: 0.01 mg to 1,000 g per day.

N-acetyl-L-tyrosine: 0.01 mg to 1,000 g per day.

Caffeine: 0.01 mg to 1,000 g per day.

*Lycium* plants or extracted *Lycium* plants: 0.001 mg to 10,000 g per day.

The following examples describing preferred materials and methodology are offered for illustrative purposes only, and are not intended to limit the scope of the present invention.

III. Examples

Example 1

A Randomized, Double-Blind, Placebo-Controlled Human Clinical Study

This example describes a randomized, double-blind, placebo-controlled human clinical study which examined the effect of orally consumed Product containing dietary fiber, phenylalanine, tyrosine, tea blend (green, black, Oolong, white, and any other tea), and goji berry, *Lycium barbarum*, as a standardized juice (GoChi) in healthy adults on resting metabolic rate (RMR) and waist circumference after consuming 60 ml (2 oz) of the Product twice a day for 14 days. The Product was separately consumed right before breakfast and lunch. Data were statistically analyzed for changes between Days 1, 8, and 15.

After one week, the RMR in the Product group (n=12) significantly increased by 270 kcal, which is about 15% of basal level (1,800 kcal). This was statistically higher than the placebo group after the same time period (FIG. 1). The RMR in a group that consumed a half dose of the Product (n=9) increased about 200 kcal over basal level. The Placebo group increased RMR by 150 kcal, which is about 8% of basal level. Thus, the Product shows over 75% increase in the body's calorie burning potential compared to placebo.

Figure 2:
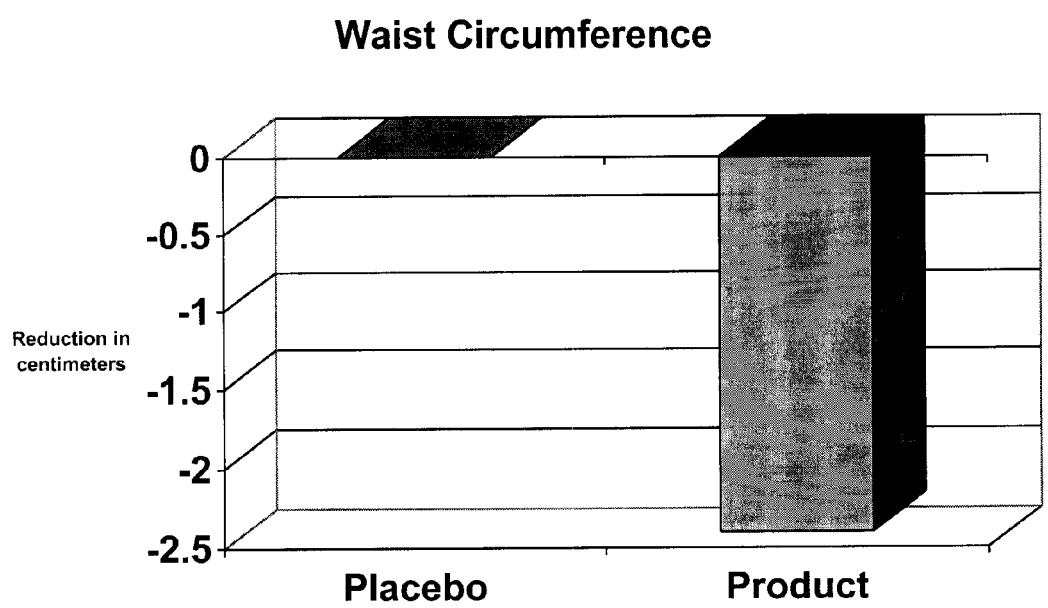
FIG. 2. Changes of waist circumference (cm) in placebo or Product groups 2 weeks after consumption.

Waist circumference in the Product group on day 15 has been reduced by 2.4 cm on Day 15, whereas the placebo group did not show a difference in waist circumference from Day 1 (FIG. 2).

These results clearly indicate that daily consumption of the Product for 14 days increases RMR and reduces waist circumference, which are related to weight control.

Example 2

Comparison Between Product and Green Tea

A comparison of Product and green tea on resting metabolic rate (RMR) by a clinical trial on kinetic effects is provided in this example. Each value indicates changes from baseline RMR.

TABLE 1

| Time after intake | Product | Green Tea |
|---|---|---|
| 10 min | 210 kcal | 80 kcal |
| 60 min | 230 kcal | 170 kcal |
| 120 min | 210 kcal | 40 kcal |
| 240 min | 210 kcal | N/A* |

(*This measurement was terminated because the RMR returned to the baseline level after two hours.)

Subjects consumed a cup of strong green tea in the morning after over 12 hours of fasting. During the fast subjects were only allowed to consume water. Five grams of high quality green tea was brewed and extracted for about 10 minutes. As shown in Table 1, the RMR values for the Product were significantly higher than the values for green tea.

Other embodiments and uses of the invention will be apparent to those skilled in the art from consideration of the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

What is claimed is:

1. A method of weight control in a subject, comprising administering a composition comprising dietary fiber, phenylalanine, tyrosine, tea blend, caffeine, and *Lycium* plants or *Lycium* plant extract preparations to said subject, whereby said subject's resting metabolic rate is increased within ten minutes of the administration such that said subject achieves weight control, wherein the increased resting metabolic rate lasts longer than four hours.

2. The method according to claim 1, wherein the *Lycium* plant extract preparation is goji juice.

3. A method of weight control in a subject, comprising administering a composition comprising dietary fiber, phenylalanine, tyrosine, tea blend, caffeine and *Lycium* plants or *Lycium* plant extract preparations to said subject, whereby said subject's waist circumference is reduced such that said subject achieves weight control.

4. The method according to claim 3, wherein the *Lycium* plant extract preparation is goji juice.

* * * * *